(12) United States Patent
Jackson et al.

(10) Patent No.: US 11,846,628 B2
(45) Date of Patent: Dec. 19, 2023

(54) ORGANELLE-TARGETED GENETICALLY-ENCODED VOLTAGE INDICATORS AND METHODS OF USE THEREOF

(71) Applicant: Wisconsin Alumni Research Foundation, Madison, WI (US)

(72) Inventors: Meyer Jackson, Madison, WI (US); Masoud Sepehri Rad, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 17/893,530

(22) Filed: Aug. 23, 2022

(65) Prior Publication Data

US 2023/0228737 A1    Jul. 20, 2023

Related U.S. Application Data

(60) Provisional application No. 63/236,028, filed on Aug. 23, 2021.

(51) Int. Cl.
*G01N 33/50* (2006.01)
*C07K 14/705* (2006.01)
*C12N 9/02* (2006.01)

(52) U.S. Cl.
CPC ......... *G01N 33/502* (2013.01); *C07K 14/705* (2013.01); *C12N 9/0071* (2013.01); *C12Y 114/14001* (2013.01); *G01N 33/5076* (2013.01); *C07K 2319/03* (2013.01); *C07K 2319/60* (2013.01)

(58) Field of Classification Search
None
See application file for complete search history.

(56) References Cited

U.S. PATENT DOCUMENTS 7,115,401 B2    10/2006  Tsien et al.
7,897,394 B2 *   3/2011  Reed ................. A01K 67/0275
                                                435/254.11

OTHER PUBLICATIONS

Chanda, B. et al.; "A hybrid approach to measuring electrical activity in genetically specified neurons"; Nature Neuroscience, vol. 8, Issue No. 11; 2005; pp. 1619-1626.
Gonzalez, J. et al.; "Voltage Sensing by Fluorescence Resonance Energy Transfer in Single Cells"; Biophysical Journal, vol. 69; 1995; pp. 1272-1280.
Scaduto, R. et al.; "Measurement of mitochondrial membrane potential using fluorescent rhodamine derivatives"; Biophysical Journal, vol. 76; 1999; pp. 469-477.
Sepheri Rad, M. et al.; "Monitoring voltage fluctuations of intracellular membranes"; Scientific Reports, vol. 8, Article No. 6911; 2018; 9 pages.
Wang, D. et al.; "Improved Probes for Hybrid Voltage Sensor Imaging"; Biophysical Journal, vol. 99; 2010; pp. 2355-2365.

* cited by examiner

*Primary Examiner* — Suzanne M Noakes
*Assistant Examiner* — Jae W Lee
(74) *Attorney, Agent, or Firm* — Karen A. LeCuyer; DeWitt LLP

(57) ABSTRACT

As described herein, a hybrid voltage sensor genetically-encoded voltage indicator (GEVI) for mitochondria or endoplasmic reticulum includes a transmembrane domain, and a fluorescent protein, wherein a terminus of the transmembrane domain and a terminus of the fluorescent protein are covalently linked directly or by a linker comprising 1 to 20 amino acids, and wherein the transmembrane domain comprises SEQ ID NO: 1, SEQ ID NO: 2, SEQ ID NO: 3, SEQ ID NO: 4 or a peptide with greater than 85%, 90%, 95% or 98% identity to SEQ ID NO: 1, SEQ ID NO: 2, SEQ ID NO: 3 or SEQ ID NO: 4. Also described are expression vectors, expression cassettes, and organelle membranes, as well as methods of determining the voltage across an organelle using the GEVIs.

18 Claims, 3 Drawing Sheets

Specification includes a Sequence Listing.

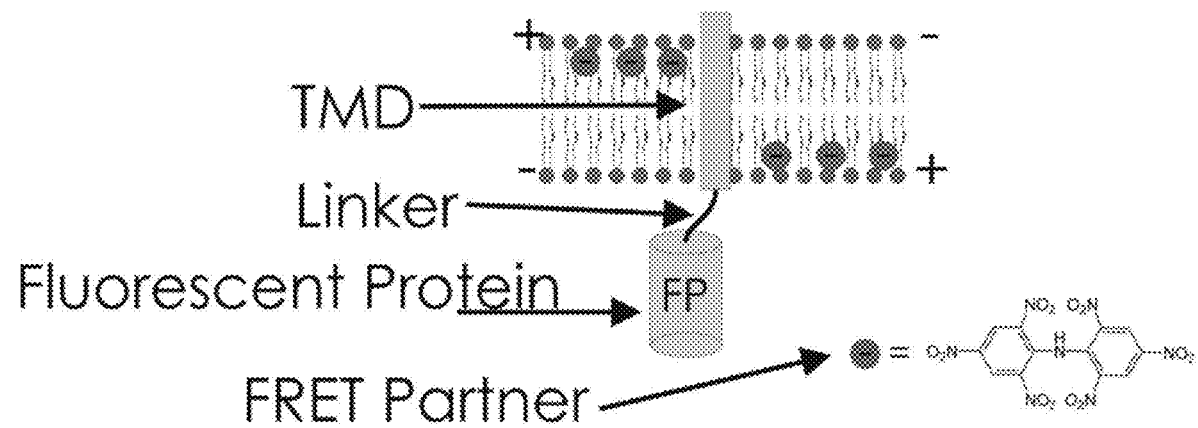
FIG. 1
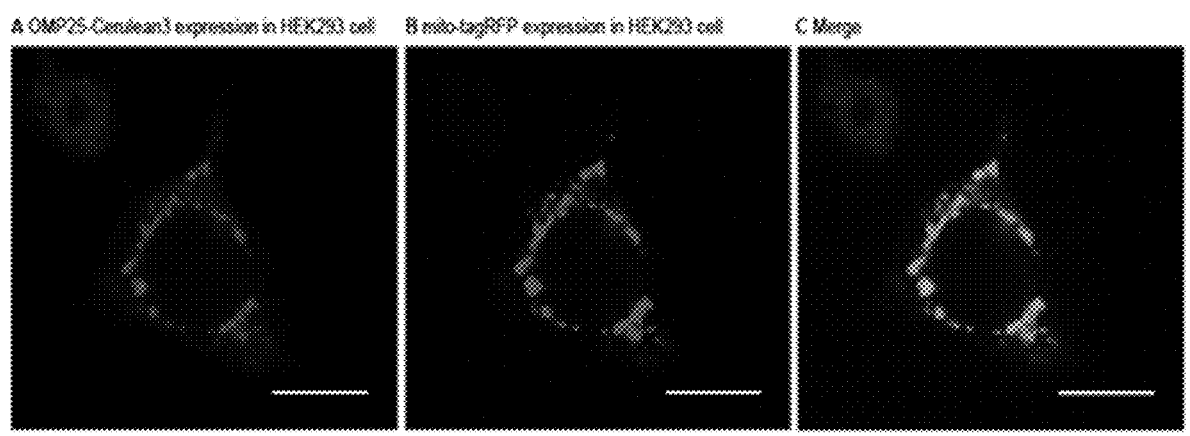
FIG. 2 A-C

FIG. 3
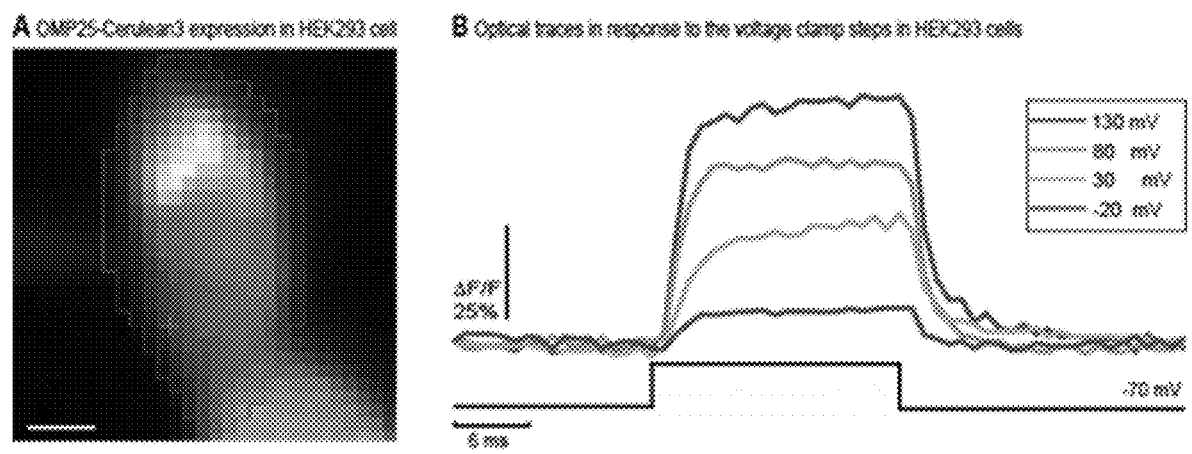
FIG. 4A-B

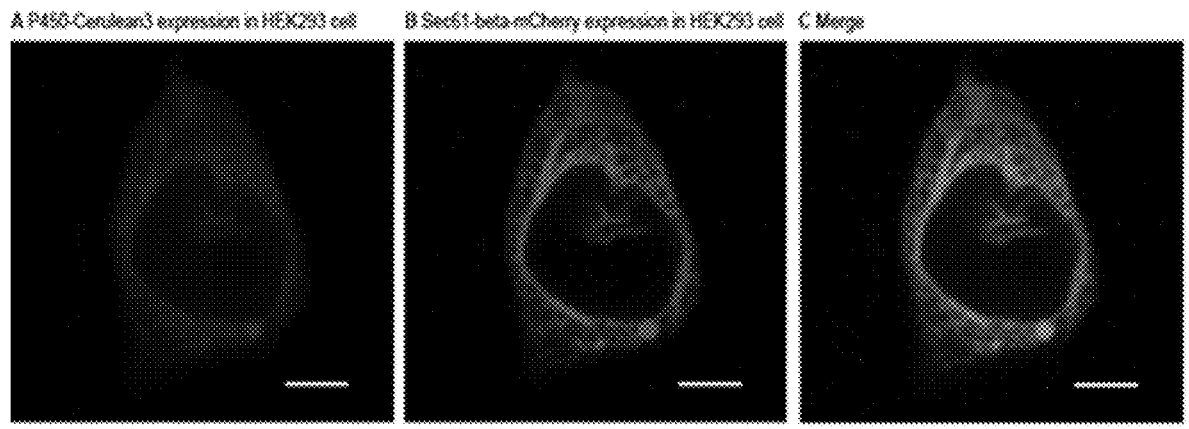
FIG. 5A-C
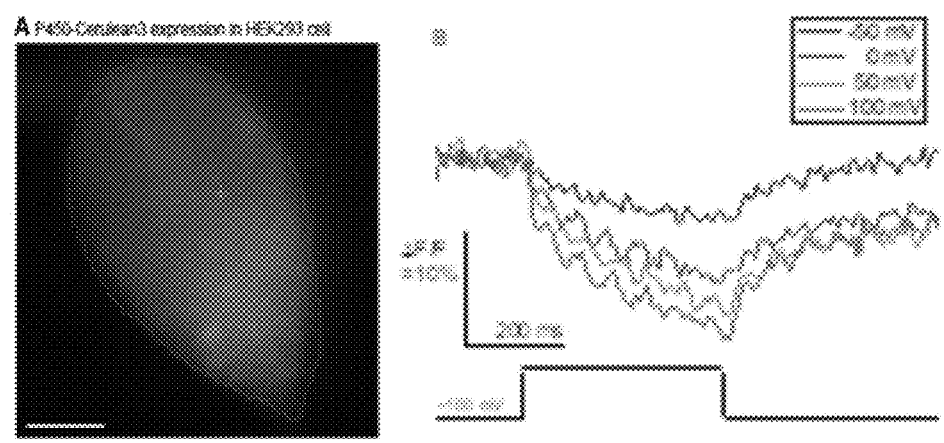
FIG. 6A-B

```
                         SEQUENCE LISTING

Sequence total quantity: 13
SEQ ID NO: 1            moltype = AA  length = 33
FEATURE                 Location/Qualifiers
source                  1..33
                        mol_type = protein
                        note = 33 residues at the C-terminus of OMP25
                        organism = synthetic construct
SEQUENCE: 1
GSKRGVPVAV VLLPVFALTL VAVWAFVRYR KQL                               33

SEQ ID NO: 2            moltype = AA  length = 27
FEATURE                 Location/Qualifiers
source                  1..27
                        mol_type = protein
                        note = N-terminal 27 residues of cytochrome P450
                        organism = synthetic construct
SEQUENCE: 2
MDPVVVLGLC LSCLLLLSLW KQSYGGG                                      27

SEQ ID NO: 3            moltype = AA  length = 26
FEATURE                 Location/Qualifiers
source                  1..26
                        mol_type = protein
                        note = motif that binds to a perimitochondrial matrix
                          protein in the organelle membrane
                        organism = synthetic construct
SEQUENCE: 3
MRSVCSLFRY RQRFPVLANS KKRCFS                                       26

SEQ ID NO: 4            moltype = AA  length = 23
FEATURE                 Location/Qualifiers
source                  1..23
                        mol_type = protein
                        note = motif that binds to a perimitochondrial matrix
                          protein in the organelle membrane
                        organism = synthetic construct
SEQUENCE: 4
ELIKPWHKTV LTGFGMTLCA VPI                                          23
```

```
SEQ ID NO: 5               moltype = AA  length = 32
FEATURE                    Location/Qualifiers
source                     1..32
                           mol_type = protein
                           note = Mito (Cox8)
                           organism = synthetic construct
SEQUENCE: 5
MSVLTPLLLR GLTGSARRLP VPRAKIHSLG DP                              32

SEQ ID NO: 6               moltype = AA  length = 26
FEATURE                    Location/Qualifiers
source                     1..26
                           mol_type = protein
                           note = OMP25-tuncated
                           organism = synthetic construct
SEQUENCE: 6
GSKRGVPVAV VLLPVFALTL VAVWAF                                     26

SEQ ID NO: 7               moltype = AA  length = 34
FEATURE                    Location/Qualifiers
source                     1..34
                           mol_type = protein
                           note = OMM(Tom20)
                           organism = synthetic construct
SEQUENCE: 7
MVGRNSAIAA GVCGALFIGY CIYFDRKRRS DPNF                            34

SEQ ID NO: 8               moltype = AA  length = 32
FEATURE                    Location/Qualifiers
source                     1..32
                           mol_type = protein
                           note = OMM(MAVS)
                           organism = synthetic construct
SEQUENCE: 8
MRPSPGALWL QVAVTGVLVV TLLVVLYRRR LH                              32

SEQ ID NO: 9               moltype = AA  length = 49
FEATURE                    Location/Qualifiers
source                     1..49
                           mol_type = protein
                           note = Intermembrane space targeting motif (SMAC)
                           organism = synthetic construct
SEQUENCE: 9
MRSVCSLFRY RQRFPVLANS KKRCFSELIK PWHKTVLTGF GMTLCAVPI             49

SEQ ID NO: 10              moltype = AA  length = 27
FEATURE                    Location/Qualifiers
source                     1..27
                           mol_type = protein
                           note = P450(pos5) truncated
                           organism = synthetic construct
SEQUENCE: 10
MDPVVVLGLC LSCLLLLSLW KRSRRRR                                    27

SEQ ID NO: 11              moltype = AA  length = 98
FEATURE                    Location/Qualifiers
source                     1..98
                           mol_type = protein
                           note = Sec61-beta
                           organism = synthetic construct
SEQUENCE: 11
RSMPGPTPSG TNVGSSGRSP SKAVAARAAG STVRQRKNAS CGTRSAGRTT SAGTGGMWRF 60
YTEDSPGLKV GPVPVLVMSL LFIASVFMLH IWGKYTRS                        98

SEQ ID NO: 12              moltype = AA  length = 35
FEATURE                    Location/Qualifiers
source                     1..35
                           mol_type = protein
                           note = ERM(Cb5)
                           organism = synthetic construct
SEQUENCE: 12
ITTVESNSSW WTNWVIPAIS ALVVALMYRL YMAED                           35
```

```
SEQ ID NO: 13          moltype = AA  length = 33
FEATURE                Location/Qualifiers
source                 1..33
                       mol_type = protein
                       note = SQS
                       organism = synthetic construct
SEQUENCE: 13
SRSHYSPIYL SFVMLLAALS WQYLTTLSQV TED                                         33
```

ORGANELLE-TARGETED GENETICALLY-ENCODED VOLTAGE INDICATORS AND METHODS OF USE THEREOF

CROSS-REFERENCE TO RELATED APPLICATIONS

This application claims priority to U.S. Provisional Application 63/236,028 filed on Aug. 23, 2021, which is incorporated herein by reference in its entirety.

STATEMENT REGARDING FEDERALLY SPONSORED RESEARCH & DEVELOPMENT

This invention was made with government support under NS093866 and NS103206 awarded by the National Institutes of Health. The government has certain rights in the invention.

SEQUENCE LISTING

The Instant Application contains a Sequence Listing which has been submitted electronically in XML format and is hereby incorporated by reference in its entirety. Said XML copy, created on Aug. 17, 2022 is named "WIS0063US2" and is 15,188 bytes in size.

BACKGROUND

Mitochondria and endoplasmic reticulum (ER) are delimited by membranes with essential roles in their biological functions. These membranes have voltage gradients that can vary and influence how these organelles carry out many of their tasks. Mitochondria have a voltage gradient across their inner membrane that is coupled to the ATP-producing electron transport chain. This voltage is the most important factor in determining mitochondrial capacity for energy generation and constitutes a key index of metabolic health. The ER membrane has pumps and channels that transport ions, but the role of voltage in controlling ER ion flux has received very little attention. Mitochondria and ER dysfunction underlie many diseases, and the role of their membranes in pathological conditions is poorly understood. While voltage at the plasma membrane of a cell can be readily measured, methods of studying the internal electrical signals of mitochondrial membranes are very limited, and there are essentially no practical methods available for the study of ER membrane potential. The inaccessibility of mitochondrial and ER membranes to electrical measurement has resulted in an enormous gap in our understanding of a wide range of normal and pathological cellular processes.

What is needed are novel genetically-encoded plasma membrane voltage indicators (GEVIs) to serve as mitochondrial voltage indicators and ER voltage indicators.

BRIEF SUMMARY

In an aspect, a hybrid voltage sensor genetically-encoded voltage indicator (GEVI) comprises a transmembrane domain, and a fluorescent protein, wherein a terminus of the transmembrane domain and a terminus of the fluorescent protein are covalently linked directly or by a linker comprising 1 to 20 amino acids, and wherein the transmembrane domain comprises SEQ ID NO: 1, SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 11, SEQ ID NO: 12, or a peptide with greater than 85%, 90%, 95% or 98% identity to SEQ ID NO: 1, SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 11, or SEQ ID NO: 12.

In another aspect, an expression vector or an expression cassette comprises a polynucleotide encoding the GEVI described above.

In a further aspect, an organelle membrane comprises the GEVI, the expression vector comprising a polynucleotide encoding the GEVI, or cassette comprising a polynucleotide encoding the GEVI.

In an aspect, a method of determining the voltage across an organelle membrane comprises expressing the GEVI in the organelle membrane, or delivering the GEVI to the organelle membrane, contacting the organelle membrane with a FRET partner for the fluorescent protein of the GEVI, applying a voltage to the plasma membrane, and recording a voltage change across the organelle membrane by patch-clamp fluorometry of the fluorescent protein-FRET partner.

BRIEF DESCRIPTION OF THE DRAWINGS

FIG. 1 is a schematic of an embodiment of a hybrid voltage sensor type of GEVI.

FIG. 2A-C show targeting OMP25-CeFP to mitochondria. Confocal images of an HEK293 cell co-expressing OMP25-CeFP (2A) and mito-tagRFP (2B) reveal a pattern of small mitochondrion-sized particles throughout the cytoplasm and excluded from the nucleus. Merged images show efficient co-localization (C). Note the absence of plasma membrane labeling. Scale bars 10 μm.

FIG. 3 shows that OMP25-PS-CFP2 does not target the plasma membrane, labeled with lck-PA-mCherry1. The super-resolution PALM images show now overlap of the two labels, indicating that a mitochondrial-targeted probe will not report unwanted voltage changes arising from the plasma membrane.

FIG. 4A-B shows mito-GEVI voltage response. HEK 293 cells expressing OMP25-CeFP. 4A shows resting fluorescence image with a faint outline around the region selected for display in B (scale bar 5 μm). 4B shows the cell was patch clamped and voltage pulses (black trace below) elicited changes in fluorescence (pulse amplitudes range from a holding potential of −70 mV). Images acquired at 1000 Hz. DPA=4 μM. Temperature 20° C.

FIG. 5A-C show colocalization of P450-CeFP with mCherry-Sec61β. Confocal images of HEK293 cells co-expressing P450-CeFP (4A) and mCherry-Sec61β (4B). Merged images (4C) show efficient colocalization. Scale bars 5 μm.

FIG. 6A-B show ER-GEVI voltage response. 5A shows resting fluorescence of an HEK 293 cell expressing P450-CeFP. A faint red curve outlines the region for display in B (scale bar 5 μm). 5B. Voltage steps (black trace below) elicit changes in fluorescence (inset indicates voltages of pulses; holding potential −100 mV). Images acquired at 200 Hz. Traces smoothed with 5-point binomial filter. Temperature 20° C. DPA=4 μM.

The above-described and other features will be appreciated and understood by those skilled in the art from the following detailed description, drawings, and appended claims.

DETAILED DESCRIPTION

Described herein are hybrid voltage sensors (hVOS), in which membrane targeting functions are clearly delineated from voltage sensing functions. The inventors used hVOS probes as GEVIs to serve as mitochondrial voltage indicators and ER voltage indicators. Preliminary data in cultured cells indicate that these probes target mitochondria and ER with very high efficiency and produce robust fluorescence changes in response to voltage steps. These probes will have wide ranging applications in basic biomedical research, and to the study of disease models. They will be especially useful in screening drugs that target organelle function.

In an aspect, an hVOS type of GEVI comprises a transmembrane domain, and a fluorescent protein, wherein a terminus of the transmembrane domain and a terminus of the fluorescent protein are covalently linked directly or by a linker, and wherein the transmembrane domain comprises SEQ ID NO: 1, SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 11, SEQ ID NO: 12, or a peptide with greater than 85%, 90%, 95% or 98% identity to SEQ ID NO: 1, SEQ ID NO: 2, SEQ ID NO: 3, SEQ ID NO: 4, SEQ ID NO: 6, SEQ ID NO: 7, SEQ ID NO: 8, SEQ ID NO: 9, SEQ ID NO: 11, or SEQ ID NO: 12.

GSKRGVPVAVVLLPVFALTLVAVWAFVRYRKQL (SEQ ID NO: 1)

MDPVVVLGLCLSCLLLLSLWKQSYGGG (SEQ ID NO: 2)

MRSVCSLFRYRQRFPVLANSKKRCFS (SEQ ID NO: 3)

ELIKPWHKTVLTGFGMTLCAVPI. (SEQ ID NO: 4)

SEQ ID NO: 1 is the 33 residues at the C-terminus of OMP25 which targets the mitochondrial membrane. SEQ ID NO: 2 is the N-terminal 27 residues of cytochrome P450 which targets the ER membrane. SEQ ID NOs. 3 and 4 are motifs that bind to a perimitochondrial matrix protein in the organelle membrane such as that from SMAC. SEQ ID NO: 6 is a truncation of OMP25. OMM(Tom20) (SEQ ID NO: 7) is a major receptor of the mitochondrial preprotein translocation system that is bound to the outer mitochondrial membrane. OMM(MAVS) (SEQ ID NO: 8) is the mitochondrial antiviral signaling protein located in the outer mitochondrial membrane. SMAC (SEQ ID NO: 9) is SMAC is a motif that targets the protein matrix of perimitochondrial space between the inner and outer membranes. SEC61 (SEQ ID NO: 11) is a component of the translocon of the ER membrane. ERM(Cb5) (SEQ ID NO:12) is the 35 amino acid carboxy terminus of cytochomr b5 and is a known ER-targeting sequence. SQS (SEQ ID NO: 13) is squalene synthase, which is an ER-resident enzyme.

As used herein, the terms "identical" or percent sequence "identity" in the context of two or more proteins, refer to two or more sequences or subsequences that are the same or have a specified percentage of amino acid residues that are the same, when compared and aligned (introducing gaps, if necessary) for maximum correspondence. The percent identity can be measured using sequence comparison software or algorithms or by visual inspection. Various algorithms and software are known in the art that can be used to obtain alignments of amino acid sequences The percent sequence identity "X" of a first amino acid sequence to a second sequence amino acid is calculated as 100 times (Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

In an aspect, a sequence with a specified percentage of sequence identity includes conservative amino acid substitutions.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., asparagine, glutamine, serine, threonine, tyrosine, cysteine), nonpolar side chains (e.g., glycine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In an aspect, the transmembrane domain comprises only conservative amino acid substitutions.

In an aspect, the fluorescent protein has an emission maximum between 400 and 550 nm. Exemplary fluorescent proteins include green fluorescent protein (GFP), enhanced GFP (eGFP), farnesylated enhanced GFP (eGFP-F), cerulean fluorescent protein (CeFP), teal fluorescent protein (TeFP), enhanced cyan fluorescent protein (ECFP), enhanced yellow fluorescent protein (EYFP), mTurquoise fluorescent protein, or mTagBFP monomeric blue fluorescent protein.

A terminus of the transmembrane domain and a terminus of the fluorescent protein are covalently linked directly or by a linker. The linker can maintain a certain minimum proximity between the terminus of the transmembrane domain and a terminus of the fluorescent protein and ensures efficient energy transfer between the fluorescent protein and fluorescence resonance energy transfer (FRET) partner when they are on the same side of the membrane, even at low concentrations. In an aspect, the linker comprises 1 to 20 amino acids.

In an aspect, the GEVI is in electrical communication with a FRET partner for the fluorescent protein. In an aspect, the FRET partner for the fluorescent protein is dipicrylamine (DPA), a (thio)barbiturate oxonol such as DiSBA-$C_2$, or 4-amino-4'-nitroazobenzene (D3).

In an aspect, the FRET partner has an absorption peak between 350 and 550 nm.

DPA is a nonfluorescent absorber with an absorption maximum of 420 nm, and it has spectral overlap with the emission of fluorescent proteins such as GFP and CeFP. Depending on the membrane potential, DPA molecules can be distributed between the outer and inner faces if a lipid membrane. At a resting membrane potential, the negatively-charged DPA molecules are mostly in the outer face of the membrane, so the emission of the fluorescent protein is unquenched. Upon membrane depolarization, the DPA molecules translate from the outside to the inside of the membrane. The closer proximity enables the DPA to quench the fluorescence of the fluorescent protein by FRET.

The term "polymethine oxonol" refers to molecules comprising two potentially acidic groups linked via a polymethine chain and possessing a single negative charge delocalized between the two acidic groups. The preferred acidic groups are barbiturates or thiobarbiturates. They may be symmetric or asymmetric, i.e., each of the two (thio)barbiturates may be the same or different. The symmetric (thio) barbiturate oxonols are described by the conventional shorthand DiBA-$C_n$-(x) and DiSBA-$C_n$-(x), where DiBA refers to the presence of two barbiturates, DiSBA refers to the presence of two thiobarbiturates, $C_n$ represents alkyl substituents having n carbon atoms on the nitrogen atoms of the (thio) barbiturates, and x denotes the number of carbon atoms in the polymethine chain linking the (thio)barbiturates. Exemplary symmetric (thio)barbiturate oxonols include DiSBA-$C_2$-(3), DiSBA-$C_6$-(3), DiSBA-$C_{10}$-(3), DiSBA-$C_4$-(3).

D3 is 4-amino-4'-nitroazobenzene, also known as Disperse Orange 3.

In an aspect, as shown in FIG. 1, the transmembrane domain of the GEVI spans the mitochondrial inner or outer membranes, or endoplasmic reticulum membrane and places the fluorescent protein at the edge of the membrane, or in the case of mitochondria, in the perimitochondrial space. In a specific aspect, the FRET partner for the fluorescent protein partitions within a mitochondrial or endoplasmic reticulum membrane.

Advantageously, the GEVI exhibits no measurable fluorescence in a plasma membrane.

Also included herein is an expression vector comprising an expression cassette for the GEVIs described herein.

The terms "expression vector" or "vector" as used herein refers to nucleic acid molecules, typically DNA, to which nucleic acid fragments encoding a GEVI can be propagated. A vector will typically contain one or more unique restriction sites and may be capable of autonomous replication in a defined host cell or vehicle organism such that the cloned sequence is reproducible. A vector may also contain a selection marker, such as, e.g., an antibiotic resistance gene, to allow selection of recipient cells that contain the vector. Vectors may include, without limitation, plasmids, phagemids, bacteriophages, bacteriophage-derived vectors, PAC, BAC, linear nucleic acids, e.g., linear DNA, viral vectors, etc., as appropriate. Expression vectors are generally configured to allow for and/or effect the expression of nucleic acids or ORFs introduced thereto in a desired expression system, e.g., in vitro, in a host cell, host organ and/or host organism. For example, expression vectors may advantageously comprise regulatory sequences.

An expression cassette contains a promoter that starts transcription of a gene, the gene itself, and a transcription termination sequence.

As used herein, the term "promoter" refers to a DNA sequence that enables a gene to be transcribed. A promoter is recognized by RNA polymerase, which then initiates transcription. Thus, a promoter contains a DNA sequence that is either bound directly by, or is involved in the recruitment, of RNA polymerase. A promoter sequence can also include "enhancer regions", which are one or more regions of DNA that can be bound with proteins (namely the trans-acting factors) to enhance transcription levels of genes in a gene-cluster. The enhancer, while typically at the 5' end of a coding region, can also be separate from a promoter sequence, e.g., can be within an intronic region of a gene or 3' to the coding region of the gene.

An "operable linkage" is a linkage in which regulatory sequences and sequences sought to be expressed are connected in such a way as to permit said expression. For example, sequences, such as, e.g., a promoter and an ORF, may be said to be operably linked if the nature of the linkage between said sequences does not: (1) result in the introduction of a frame-shift mutation, (2) interfere with the ability of the promoter to direct the transcription of the ORF, (3) interfere with the ability of the ORF to be transcribed from the promoter sequence. Hence, "operably linked" may mean incorporated into a genetic construct so that expression control sequences, such as a promoter, effectively control expression of a coding sequence of interest, such as the nucleic acid molecule as defined herein.

The promotor may be a constitutive or inducible (conditional) promoter. A constitutive promoter is understood to be a promoter whose expression is constant under the standard culturing conditions. Inducible promoters are promoters that are responsive to one or more induction cues. For example, an inducible promoter can be chemically regulated (e.g., a promoter whose transcriptional activity is regulated by the presence or absence of a chemical inducing agent such as an alcohol, tetracycline, a steroid, a metal, or other small molecule such as tamoxifen) or physically regulated (e.g., a promoter whose transcriptional activity is regulated by the presence or absence of a physical inducer such as light or high or low temperatures). An inducible promoter can also be indirectly regulated by one or more transcription factors that are themselves directly regulated by chemical or physical cues.

In an aspect, a method of determining the voltage across an organelle membrane in a cell comprises expressing the GEVI in the organelle membrane, or delivering the GEVI to the organelle membrane, contacting the organelle membrane with a FRET partner for the fluorescent protein of the GEVI, applying a voltage to the plasma membrane of the cell, and recording a voltage change across the organelle membrane by patch-clamp fluorometry of the fluorescent protein-FRET partner.

An expression vector or expression cassette can be delivered to a specific cell type by a targeted viral vector. Targeted viral vectors can be prepared by pseudotyping (transferring viral attachment proteins), using adaptor proteins (dual specific molecules that bind both a viral attachment protein and a receptor on a target cell), genetic incorporation of targeting ligands, and the like. Adaptor proteins include receptor-ligand complexes, chemically conjugated adaptors, avidin/biotin, camelid nanobodies, and monoclonal antibodies, for example.

A GEVI encoded by the expression vector or cassette can be delivered to the organelle membrane by an organelle-specific targeting motif such as a canonical mitochondrial localization signal, or an ER signal sequence (a sequence of at least eight hydrophobic residues at the amino terminus of a peptide).

The patch-clamp technique allows one to measure the ion currents flowing through membranes. The patch-clamp fluorometry technique (PCF), an approach combining fluorescence recordings and patch-clamp recordings, permits the simultaneous correlation of ionic current recordings with the activity of protein conformational changes reported by the fluorescence measurement. An exemplary experimental set-up comprises an Olympus BX51 microscope and a CCD-SMQ camera or a DaVinci 2K camera. The CCD-SMQ acquires images at up to 2 kHz with a resolution of 80×80; the DaVinci 2K has higher speed and resolution. A Prizmatix LED UHP-F-HCRI white light source can be used to provide strong and stable excitation in the critical spectral bands and excite multiple probes. An assortment of high NA objectives with magnifications ranging from 10× to 60× can be used. Patch clamping can be performed with an Axopatch 200B, a Digidata interface, a computer, and PClamp software. These set-ups can be used to patch clamp cells expressing GEVIs, apply voltage steps, and measure fluorescence responses.

In specific aspects, the GEVIs can be used for drug screening for drugs which affect the membrane potential of organelles. Detection of a change in membrane potential or membrane potential changes in response to the test agent relative to the control indicates that the test agent is active. The control can be a reference drug or no drug. Organelle membrane potentials change in response to a variety of biological challenges. In an aspect, a test agent improves mitochondrial function. Mitochondria respond to metabolic stress resulting from nutrient shortage or oxidative stress or a disruption of metabolism, or in the case of neurons, stress resulting from excessive electrical activity, glutamate, $H_2O_2$, or an NO donor. Endoplasmic reticulum membrane potentials can respond to changes in cellular calcium. A GEVI can monitor these organelle voltage changes in the presence or absence of a test agent to indicate if the test agent has an action on this organelle response. Membrane potentials and membrane potential responses can also be determined in the presence or absence of a pharmacologic agent of known activity (i.e., a standard agent) or putative activity (i.e., a test agent). A difference in membrane potentials or membrane potential responses as detected by the methods disclosed herein allows one to compare the activity of the test agent to that of the standard agent. Mitochondrial stress is a precursor to cell death in a variety of pathological conditions and their dysfunction contributes to neurodegeneration in diseases such as Alzheimer's and Parkinson's disease. A mitochondrial GEVI would be useful in screening drugs that correct mitochondrial dysfunction in the treatment of these diseases. ER stress is also associated with many pathological conditions and initiates the adverse effects of cancer chemotherapy. An ER GEVI will provide a useful readout to select chemotherapeutic agents that produce minimal ER stress.

Biological cells include, but are not limited to, primary cultures of mammalian cells, cells dissociated from mammalian tissue, either immediately or after primary culture, or cells in acute tissue preparations such as brain slices. Cell types include, but are not limited to, white blood cells (e.g., leukocytes), hepatocytes, pancreatic beta-cells, neurons, smooth muscle cells, intestinal epithelial cells, cardiac myocytes, glial cells, and the like. Cell types also can include cells derived from human stem cells.

The screening methods described herein can be made on cells growing in or deposited on solid surfaces or in suspension. A common technique is to use a microtiter plate well wherein the fluorescence measurements are made by commercially available fluorescent plate readers. The methods include high throughput screening in both automated and semiautomated systems.

In an aspect, the organelle is mitochondria, and the method further comprises contacting the cell with a test mitochondrial inhibitor, enhancer, or protective agent. In another aspect, the organelle is ER, and the method further comprises contacting the cell with a test ER inhibitor, enhancer, or protective agent.

In an aspect, the organelle membrane is in a cell that is a disease model. GEVIs that target mitochondria can be useful to study disease models and screen drugs related to neurological and neurodegenerative disorders (e.g., Alzheimer's Disease (AD), Parkinson's Disease (PD), traumatic brain injury (TBI), multiple sclerosis, muscular dystrophy, cardiomyopathy, cancer, obesity, hematopoietic dysfunction, maintenance of somatic progenitor cells, and the like. In an aspect, the disease is multiple sclerosis, and the cells comprise cerebellar Purkinje cell axons. GEVIs that target the ER can be useful to study disease models and screen drugs related to neurological disorders, muscular dystrophy, cardiomyopathy, cancer, and the like.

In another aspect, a method of determining the voltage across an organelle membrane comprises expressing a fluorescent protein tagged with a motif that binds to a perimitochondrial matrix protein residing in the space between the mitochondrial inner and outer membranes, contacting the organelle membrane with a FRET partner for the fluorescent protein. The FRET partner within the mitochondrial membrane is sufficiently close to the perimitochondrial space to enable FRET changes when the FRET partner moves within the mitochondrial membrane. Applying a voltage to the cell, and recording a voltage change across the organelle membrane by patch-clamp fluorometry of the fluorescent protein-FRET partner. The organelle GEVI reports the transmission of voltage changes from the patch-clamped plasma membrane to internal membranes of organelles. Perimitochondrial proteins include SEQ ID NO: 3 and SEQ ID NO: 4.

The invention is further illustrated by the following non-limiting examples.

EXAMPLES

Example 1: Development of a Mitochondrial GEVI

The inventors identified a motif from OMP25, a protein that targets the outer mitochondrial membrane with high efficiency. Tagging CeFP with the 33 C-terminal residues of OMP25 generated the following construct.

```
                                              (SEQ ID NO: 1)
GSKRGVPVAVVLLPVFALTLVAVWAFVRYRKQL-CeFP
```

This probe, OMP25-CeFP colocalizes with mito-tagRFP, a widely-used mitochondrial matrix label (FIG. 2A-C). No plasma membrane targeting is visible in these images, indicating that contaminating signals from plasma membrane will not be a problem. The absence of plasma membrane was confirmed by co-expressing the red plasma membrane GEVI Ilmo1 and by Ick-PA-mCherry1 (FIG. 3).

FIG. 4A-B demonstrate that OMP25-CeFP reports changes in the voltage of the inner mitochondrial membrane ($\Delta\psi_m$) This probe targets the outer membrane rather than the mitochondrial inner membrane (MIM), placing the FRET partner (FP) in the perimitochondrial space. The inner and outer membranes are separated by only approximately 5 nm, so an FP protruding into this space can undergo FRET with DPA at the outer face of the MIM. The resting $\Delta\psi_m$ of −140 mV keeps negatively charged DPA at this location. Depolarization pushes DPA across the MIM to the inner face, away from the CeFP in the intermembrane space, thus reducing FRET and increasing fluorescence. The strong targeting (FIG. 2 and FIG. 3) and voltage sensing (FIG. 4) make OMP25-CeFP a validated mito-GEVI.

The Table summarizes results of 8 other mitochondrial targeted probes tested as described for FIG. 4B. This illustrates the complex nature of probe performance. Performance cannot be predicted based on sequence, and probes must be individually tested.

TABLE 1

MEMBRANE VOLTAGE MEASUREMENTS FOR MITOCHONDRIAL AND ER CONSTRUCTS

| Construct | Signal Direction | Signal kinetics |
|---|---|---|
| Mitochondrial Constructs | | |
| Mito(Cox8)-mCerulean3<br>Comment: FP targeted to the inner membrane | No signal | |
| OMP25-Cerulean3<br>Comment: FP targeted to OMM in the intermembrane space side | Upward | Fast |
| Cerulean3-OMP25<br>Comment: FP targeted to the cytosolic side of OMM | Downward | Slow |
| OMP-truncated-Cerulean3<br>Comment: FP targeted to OMM in the intermembrane space side | Downward- Almost no signal | |
| Cerulean3-OMM(Tom20)<br>Comment: FP in the intermembrane space side of the OMM | Downward | slow |
| OMM(MAVS)-Cerulean3<br>Comment: FP in the intermembrane space side of the OMM | Downward | slow |
| Cerulean3-OMM(MAVS)<br>Comment: FP in the cytosolic side of the OMM | Downward | slow |
| Intermembrane space targeting motif-Cerulean3<br>Comment: FP in the intermembrane space | Downward- small signal | fast |
| ER Constructs | | |
| P450(pos3)-Cerulean3<br>Comment: FP in the cytosolic side of the ER membrane | No signal | |
| P450(pos5)-Cerulean3<br>Comment: FP in the cytosolic side of the ER membrane | No signal | |
| P450-Cerulean3<br>Comment: FP in the cytosolic side of the ER membrane | Downward | Slow |
| Cerulean3-P450<br>Comment 1: Expressed in the plasma membrane and ER<br>Comment 2: FP in the luminal side of the ER membrane | Downward | Slow |
| Sec61-beta-Cerulean3<br>Comment 1: Left shifted voltage sensitivity<br>Comment 2: FP in the luminal side of the ER membrane | Downward | Slow |
| Cerulean3-Sec61-beta<br>Comment: FP in the cytosolic side of the ER membrane | Downward | Slow |
| ERM(Cb5)-Cerulean3<br>Comment: FP in the luminal side of the ER membrane | Downward | Slow |
| Cerulean3-ERM(Cb5)<br>Comment: FP in the cytosolic side of the ER membrane | Downward | Slow |
| SQS-Cerulean3<br>Comment: FP in the luminal side of the ER membrane | Upward Small signal | Very fast |

TABLE 2

CONSTRUCT DESIGN

| | |
|---|---|
| Mitochondrial Construct Design | |
| Mito(Cox8)-Cerulean3 | MSVLTPLLLRGLTGSARRLPVPRAKIHSLG-DP-Cerulean3<br>SEQ ID NO: 5 |
| OMP25-Cerulean3 | GSKRGVPVAVVLLPVFALTLVAVWAFVRYRKQL-Cerulean3<br>SEQ ID NO: 1 |
| Cerulean3-OMP25 | Cerulean3-GSKRGVPVAVVLLPVFALTLVAVWAFVRYRKQL<br>SEQ ID NO: 1 |
| OMP25-truncated-Cerulean3 | GSKRGVPVAVVLLPVFALTLVAVWAF-Cerulean3<br>SEQ ID NO: 6 |
| Cerulean3-OMM(Tom20) | Cerulean3-MVGRNSAIAAGVCGALFIGYCIYFDRKRRSDPNF<br>SEQ ID NO: 7 |
| OMM(MAVS)-Cerulean3 | MRPSPGALWLQVAVTGVLVVTLLVVLYRRRLH-Cerulean3<br>SEQ ID NO: 8 |
| Cerulean3-OMM(MAVS) | Cerulean3-MRPSPGALWLQVAVTGVLVVTLLVVLYRRRLH<br>SEQ ID NO: 8 |
| Intermembrane space targeting motif (SMAC)-Cerulean3 | MRSVCSLFRYRQRFPVLANSKKRCFSELIKPWHKTVLTGFG MTLCAVPI-Cerulean3<br>SEQ ID NO: 9 |
| ER Construct Design | |
| P450(pos5)-Cerulean3 | MDPVVVLGLCLSCLLLLSLWKRSRRRR-Cerulean3<br>SEQ ID NO: 10 |
| P450-Cerulean3 | MDPVVVLGLCLSCLLLLSLWKQSYGGG-Cerulean3<br>SEQ ID NO: 2 |

TABLE 2-continued

CONSTRUCT DESIGN

| | |
|---|---|
| Cerulean3-P450 | Cerulean3-MDPVVVLGLCLSCLLLLSLWKQSYGGG<br>SEQ ID NO: 2 |
| Sec61-beta-<br>Cerulean3 | RSMPGPTPSGTNVGSSGRSPSKAVAARAAGSTVRQRKNASC<br>GTRSAGRTTSAGTGGMWRFYTEDSPGLKVGPVPVLVMSLL<br>FIASVFMLHIWGKYTRS-Cerulean3<br>SEQ ID NO: 11 |
| Cerulean3-Sec61-<br>beta | Cerulean3-<br>RSMPGPTPSGTNVGSSGRSPSKAVAARAAGSTVRQRKNASC<br>GTRSAGRTTSAGTGGMWRFYTEDSPGLKVGPVPVLVMSLL<br>FIASVFMLHIWGKYTRS<br>SEQ ID NO: 11 |
| ERM(Cb5)-<br>Cerulean3 | ITTVESNSSWWTNWVIPAISALVVALMYRLYMAED-<br>Cerulean3<br>SEQ ID NO: 12 |
| Cerulean3-<br>ERM(Cb5) | Cerulean3-<br>ITTVESNSSWWTNWVIPAISALVVALMYRLYMAED<br>SEQ ID NO: 12 |
| SQS-Cerulean3 | SRSHYSPIYLSFVMLLAALSWQYLTTLSQVTED-Cerulean3<br>SEQ ID NO: 13 |

Specifically, for the mitochondrial constructs listed in the Table, OMP25 (SEQ ID NO: 1) provided a robust signal, while the construct Mito(Cox8) and truncated OMP25 provided no or almost no signal. Other constructs produced variable results. For example, constructs OMM(Tom 20) and OMM (MAVS) produced slow downward signals, and intermembrane space targeting motif produced a small, fast, downward signal.

In addition to CeFP, other FPs can be employed. For a variety of tethers, the best FPs were on the blue-green side of the visible spectrum. CeFP was selected, and a brighter version of CeFP with dramatically improved photostability can be employed. The tethers used for mito-GEVIs can alter the FRET interaction with DPA, so other blue-green FPs with longer and shorter excitation maxima will be tested to determine whether increases or decreases in Ro for FP-DPA FRET improve voltage sensor performance. For plasma membrane sensing, EGFP, TealFP, and mTurquoise are within 20-30% of CeFP in AF/F and they can be tested in organelle-targeted probes. mTagBFP will also be tested because of its high brightness and blue-shifted excitation (peak 402 nm), which should shorten Ro for FRET with DPA.

Different FRET partners will affect the voltage sensing ability of the GEVIs, so the mito-GEVIs can be tested with two other FRET partners, D3 and DiSBA-$C_2$-(3). D3 has a peak absorbance at approximately 440 nm, with a shoulder that overlaps substantially with CeFP emission. DiSBA-$C_2$-(3) is available from ThermoFischer and has an excitation peak at 540 nm and an emission peak at 560 nm, so we will test this FRET partner in a mito-GEVI containing EGFP or YFP. Because DiSBA-$C_2$-(3) transits the membrane slowly compared to DPA, we will increase pulse duration, and weigh the disadvantage of slower response time against a possible benefit of better signal-to-noise. For each FRET partner we will compare voltage responses, signal-to-noise, and response dynamics. We will also test photostability/phototoxicity in HEK293 cells by repeated data acquisition at 5 min intervals for two hours.

Example 2: Development of an ER GEVI

The N-terminal 27 residues of cytochrome P450 serve as a determinant for exclusion from the recycling pathway. This motif harbors one TMD and has been used previously to target a genetically-encoded $Ca^{2+}$ sensor to the cytosolic face of the ER membrane.

(SEQ ID NO: 2)
MDPVVVLGLCLSCLLLLSLWKQSYGGG-CeFP

This construct, P450-CeFP, colocalizes with the ER marker mCherry-Sec61-β and displays no apparent plasma membrane targeting (FIG. 5). Preliminary data with P450-CeFP demonstrate that this probe produces fluorescence changes in response to voltage steps (FIG. 6).

The Table summarizes results of 9 other ER targeted probes tested as described for FIG. 6B. This illustrates the complex nature of probe performance Performance cannot be predicted based on sequence, and probes must be individually tested.

For the ER constructs, P450 (SEQ ID NO: 2) provided a robust signal, while truncated versions (pos3, pos5) provided no signal. Other constructs produced variable results. For example, Sec61-beta and ERM(Cb5) produced slow downward signals and SQS produced a small, fast upward signal.

CeFP is at the C-terminus of this probe, so it is at the cytoplasmic face of the ER membrane. Positive pulses drive DPA from the ER luminal membrane face to the cytoplasmic face to quench emission and reduce fluorescence. The probe response is slower than that of the mito-GEVI (FIG. 4), indicating distinct charging dynamics for the ER membrane. The largest change between −50 and 0 mV demonstrates the non-linear, sigmoidal voltage dependence, which is a general characteristic of hVOS probes.

Evaluation of FPs and FRET partners will focus on the FPs CeFP, EGFP, and mTagBFP, and the FRET partners DPA, D3 and DiSBAC$_2$. Using patch-fluorometry to evaluate ER-GEVI performance, we will systematically vary FPs and FRET.

We will assay the potential impact of an ER-GEVI on ER function by measuring $Ca^{2+}$ release fluorometrically in cells expressing an ER-GEVI. We will trigger increases in cytosolic $Ca^{2+}$ with histamine and carbachol to activate receptors in HEK293 cells and trigger IP$_3$ production. IP$_3$ activates IP$_3$ receptors to gate ER Ca$^{2+}$ channels, leading to robust rises in cytosolic Ca$^{2+}$. We will patch clamp cells with an intracellular pipette solution containing 25-50 μM Cal-590 (AAT Bioquest; K$_d$ 561 nm). This Ca$^{2+}$ dye has an excitation maximum of 574 nm, well separated from the blue-green FPs of the ER-GEVIs. We will apply carbachol or histamine and measure the magnitude and duration of the Ca$^{2+}$ transient. These measurements from control and ER-GEVI-expressing HEK293 cells will indicate whether ER-GEVI expression alters ER function. We also expect to see ER-GEVI signals in response to these ligands, because charge movement across the ER membrane should change $\Delta\psi_{ER}$.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. "About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±10% or 5% of the stated value. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A hybrid voltage sensor genetically-encoded voltage indicator (GEVI), comprising a transmembrane domain, and a fluorescent protein, wherein a terminus of the transmembrane domain and a terminus of the fluorescent protein are covalently linked directly or by a linker comprising 1 to 20 amino acids, and wherein the transmembrane domain comprises:
   SEQ ID NO: 1 or a peptide with greater than 95% sequence identity to SEQ ID NO: 1,
   SEQ ID NO: 3 or a peptide with greater than 98% sequence identity to SEQ ID NO: 3,
   SEQ ID NO: 6 or a peptide with greater than 90% sequence identity to SEQ ID NO: 6,
   SEQ ID NO: 8 or a peptide with greater than 98% sequence identity to SEQ ID NO: 8,
   SEQ ID NO: 9, or
   SEQ ID NO: 11.

2. The GEVI of claim 1, wherein the fluorescent protein has an emission maximum between 400 and 550 nm.

3. The GEVI of claim 1, wherein the fluorescent protein comprises green fluorescent protein (GFP), enhanced GFP (eGFP), farnesylated enhanced GFP (eGFP-F), cerulean fluorescent protein (CeFP), teal fluorescent protein (TeFP), enhanced cyan fluorescent protein (ECFP), enhanced yellow fluorescent protein (EYFP), mTurquoise fluorescent protein, or mTagBFP monomeric blue fluorescent protein.

4. The GEVI of claim 1, in electrical communication with a FRET partner for the fluorescent protein.

5. The GEVI of claim 4, wherein the FRET partner for the fluorescent protein is dipicrylamine (DPA), a (thio)barbiturate oxonol DiSBA-$C_2$, or 4-amino-4'-nitroazobenzene.

6. The GEVI of claim 4, wherein the transmembrane domain of the GEVI spans the mitochondrial membrane and places the fluorescent protein in the intermembrane space.

7. The GEVI of claim 4, wherein the transmembrane domain of the GEVI places the fluorescent protein at the edge of the endoplasmic reticulum membrane.

8. The GEVI of claim 4, wherein the FRET partner for the fluorescent protein is in communication with a mitochondrial inner membrane.

9. The GEVI of claim 4, wherein the FRET partner for the fluorescent protein is in communication with an endoplasmic reticulum membrane.

10. The GEVI of claim 4, wherein the FRET partner has an absorption peak and an emission peak between 350 and 550 nm.

11. An organelle membrane comprising the GEVI of claim 1.

12. A method of determining the voltage across an organelle membrane, comprising
   expressing the GEVI of claim 1 in the organelle membrane, or delivering the GEVI of claim 1 to the organelle membrane,
   contacting the organelle membrane with a FRET partner for the fluorescent protein of the GEVI,
   applying a voltage to the plasma membrane, and
   recording a voltage change across the organelle membrane by patch-clamp fluorometry of the fluorescent protein-FRET partner.

13. The method of claim 12, wherein the organelle is mitochondria, and the method further comprises contacting the cell with a test mitochondrial inhibitor, enhancer, or protective agent.

14. The method of claim 12, wherein the organelle is ER, and the method further comprises contacting the cell with a test ER inhibitor, enhancer, or protective agent.

15. The method of claim 12, wherein the organelle membrane is in a cell that is a disease model.

16. The method of claim 15, wherein the organelle is mitochondria, and the disease model is a model for Alzheimer's Disease (AD), Parkinson's Disease (PD), traumatic brain injury (TBI), multiple sclerosis, muscular dystrophy, cardiomyopathy, cancer, obesity, hematopoietic dysfunction, or maintenance of somatic progenitor cells.

17. The method of claim 15, wherein the disease is multiple sclerosis, and the cells comprise cerebellar Purkinje cell axons.

18. The method of claim 15, wherein the organelle is ER, and the disease model is a model for a neurological disorder, muscular dystrophy, cardiomyopathy, or cancer.

* * * * *